(12) United States Patent
Hansen et al.

(10) Patent No.: US 12,285,622 B2
(45) Date of Patent: Apr. 29, 2025

(54) MOBILE DEFIBRILLATOR

(71) Applicant: Defibrio AS, Raadal (NO)

(72) Inventors: Jon Kåre Hansen, Bergen (NO); Bjarte Kjell Nore, Bergen (NO); Arne Bergby, Askøy (NO)

(73) Assignee: Defibrio AS, Raadal (NO)

( * ) Notice: Subject to any disclaimer, the term of this patent is extended or adjusted under 35 U.S.C. 154(b) by 52 days.

(21) Appl. No.: 17/819,108

(22) Filed: Aug. 11, 2022

(65) Prior Publication Data

US 2022/0379129 A1 Dec. 1, 2022

Related U.S. Application Data

(62) Division of application No. 17/502,150, filed on Oct. 15, 2021, now Pat. No. 11,439,837, which is a division of application No. 16/938,275, filed on Jul. 24, 2020, now Pat. No. 11,173,315.

(51) Int. Cl.
*A61N 1/39* (2006.01)
*A61H 31/00* (2006.01)

(52) U.S. Cl.
CPC ....... *A61N 1/39044* (2017.08); *A61N 1/3918* (2013.01); *A61N 1/3987* (2013.01); *A61H 31/007* (2013.01)

(58) Field of Classification Search
CPC .............. A61N 1/39044; A61N 1/3918; A61N 1/3987; A61H 31/007
See application file for complete search history.

(56) References Cited

U.S. PATENT DOCUMENTS

| | | | |
|---|---|---|---|
| 5,658,316 | A | 8/1997 | Lamond et al. |
| 5,782,878 | A | 7/1998 | Morgan et al. |
| 6,321,113 | B1 | 11/2001 | Parker et al. |
| 6,356,785 | B1 | 3/2002 | Snyder et al. |
| 6,553,257 | B2 | 4/2003 | Snyder et al. |
| 6,813,517 | B2 | 11/2004 | Daynes et al. |
| 8,000,787 | B2 | 8/2011 | Hamilton et al. |
| 8,086,320 | B2 | 12/2011 | Saketkhou |
| 8,706,225 | B2 | 4/2014 | Matos |
| 8,725,253 | B2 | 5/2014 | Johnson et al. |
| 8,923,918 | B2 | 12/2014 | Kreger et al. |
| 9,067,080 | B2 | 6/2015 | Einy |
| 9,089,718 | B2 | 7/2015 | Owen et al. |
| 9,107,586 | B2 | 8/2015 | Tran |
| 9,138,592 | B2 | 9/2015 | Wu |
| 9,233,255 | B2 | 1/2016 | Powers |

(Continued)

FOREIGN PATENT DOCUMENTS

| | | |
|---|---|---|
| JP | 2016041239 | 3/2016 |
| JP | 2017-525410 | 9/2017 |

(Continued)

OTHER PUBLICATIONS

PCT International Application No. PCT/IB2021/056610, International Search Report and Written Opinion of the International Searching Authority, dated Oct. 20, 2021, 13 pages.

(Continued)

*Primary Examiner* — Rex R Holmes
(74) *Attorney, Agent, or Firm* — DLA PIPER LLP (US)

(57) ABSTRACT

Systems and methods for controlling a mobile defibrillator (AED) unit are provided.

18 Claims, 9 Drawing Sheets

(56) References Cited

U.S. PATENT DOCUMENTS

| | | |
|---|---|---|
| 9,242,116 B2 | 1/2016 | Shaker |
| 9,480,852 B2 | 11/2016 | Bonnamy |
| 9,504,397 B2 | 11/2016 | Khuon et al. |
| 9,636,513 B2 | 5/2017 | Kuo et al. |
| 9,717,925 B2 | 8/2017 | King et al. |
| 9,789,326 B2 | 10/2017 | Schwibner et al. |
| 9,889,311 B2 | 2/2018 | Horseman et al. |
| 10,058,709 B2 | 8/2018 | Tilton, Jr. |
| 10,112,054 B2 | 10/2018 | Beyer et al. |
| 10,146,912 B2 | 12/2018 | Drysdale et al. |
| 10,155,110 B2 | 12/2018 | Finch et al. |
| 10,213,124 B2 | 2/2019 | Freeman et al. |
| 10,213,612 B2 | 2/2019 | Nova et al. |
| 10,303,852 B2 | 5/2019 | Peterson et al. |
| 10,369,372 B2 | 8/2019 | Stadler et al. |
| 10,449,380 B2 | 10/2019 | Andrews |
| 10,537,746 B2 | 1/2020 | Snyder |
| 10,542,961 B2 | 1/2020 | Barsinmantov et al. |
| 10,589,112 B2 | 3/2020 | Quan et al. |
| 10,665,078 B1 | 5/2020 | Picco et al. |
| 10,765,873 B2 | 9/2020 | Martin et al. |
| 10,792,506 B2 | 10/2020 | Elghazzawi |
| 10,903,675 B2 | 1/2021 | Beyer et al. |
| 10,926,099 B2 | 2/2021 | Aoyama et al. |
| 10,946,209 B2 | 3/2021 | Andrews et al. |
| 10,959,683 B2 | 3/2021 | Freeman et al. |
| 10,976,908 B2 | 4/2021 | Freeman et al. |
| 11,077,312 B2 | 8/2021 | Sturman et al. |
| 11,089,989 B2 | 8/2021 | Freed et al. |
| 11,097,118 B2 | 8/2021 | Freeman et al. |
| 11,097,121 B2 | 8/2021 | Beyer et al. |
| 11,103,718 B2 | 8/2021 | Montague et al. |
| 11,109,816 B2 | 9/2021 | Martin et al. |
| 11,122,983 B2 | 9/2021 | Donnelly et al. |
| 11,141,599 B2 | 10/2021 | Chang |
| 2001/0047140 A1 | 11/2001 | Freeman |
| 2004/0064342 A1 | 4/2004 | Browne et al. |
| 2004/0204743 A1 | 10/2004 | McGrath et al. |
| 2007/0032830 A1 | 2/2007 | Bowers |
| 2008/0140140 A1 | 6/2008 | Grimley et al. |
| 2008/0177341 A1 | 7/2008 | Bowers |
| 2010/0022904 A1 | 1/2010 | Centen |
| 2013/0023781 A1 | 1/2013 | Freeman et al. |
| 2013/0085538 A1 | 4/2013 | Volpe et al. |
| 2014/0043149 A1 | 2/2014 | Cowan et al. |
| 2014/0107718 A1 | 4/2014 | Foote et al. |
| 2014/0222096 A1 | 8/2014 | Hu et al. |
| 2015/0088016 A1 | 3/2015 | Fleischacker et al. |
| 2016/0030758 A1 | 2/2016 | Guiney et al. |
| 2016/0133160 A1 | 5/2016 | Packer et al. |
| 2016/0135706 A1 | 5/2016 | Sullivan et al. |
| 2016/0193109 A1 | 7/2016 | Fleischacker et al. |
| 2016/0271408 A1 | 9/2016 | Newton et al. |
| 2016/0279405 A1 | 9/2016 | Riley et al. |
| 2017/0056682 A1 | 3/2017 | Kumar et al. |
| 2017/0087371 A1 | 3/2017 | Freeman et al. |
| 2017/0216613 A1 | 8/2017 | Kaib et al. |
| 2018/0116537 A1 | 5/2018 | Sullivan et al. |
| 2018/0169426 A1* | 6/2018 | Montague ............ A61N 1/3981 |
| 2018/0207435 A1 | 7/2018 | Yetter |
| 2019/0117989 A1 | 4/2019 | Andrews et al. |
| 2019/0247272 A1 | 8/2019 | Fleischacker et al. |
| 2019/0351245 A1 | 11/2019 | Anderson et al. |
| 2019/0385744 A1 | 12/2019 | Freeman et al. |
| 2020/0038671 A1 | 2/2020 | Schulhauser et al. |
| 2021/0093876 A1 | 4/2021 | Montague et al. |
| 2021/0308003 A1 | 10/2021 | Fleischacker et al. |
| 2022/0008030 A1* | 1/2022 | Sunshine ................ G10L 25/66 |

FOREIGN PATENT DOCUMENTS

| | | |
|---|---|---|
| JP | 2020-503916 | 2/2020 |
| JP | 2020-503920 | 2/2020 |
| WO | 2020014715 | 1/2020 |

OTHER PUBLICATIONS

Office Action for Japanese Patent Application No. 2023-504506, mailed Nov. 24, 2023, 22 Pages.

Office Action for Australian Patent Application No. 2021313870, mailed Nov. 7, 2023, 4 Pages.

Office Action for EP Patent Application No. 21755058.1, mailed Jan. 10, 2024, 5 Pages.

Notice of Acceptance for Australian Patent Application No. 2021313870, mailed Feb. 20, 2024, 3 Pages.

Notice of Allowance of Japanese Patent Application No. 2023-504506 mailed May 31, 2024, 2 pages.

Office Action of EP Patent Application No. 21755058.1, dated Jun. 4, 2024, 4 pages.

Office Action for Brazilian Patent Application No. BR112023000479-9, dated Sep. 6, 2024, 12 pages.

Office Action of EP Application No. 21755058.1 dated Aug. 26, 2024, 4 pages.

Office Action for Korean Patent Application No. 10-2023-7005843, mailed Feb. 12, 2025, 23 Pages.

* cited by examiner

MOBILE DEFIBRILLATOR

CROSS-REFERENCE TO RELATED APPLICATION INFORMATION

This is a divisional of U.S. patent application Ser. No. 17/502,150, filed Oct. 15, 2021, now U.S. Pat. No. 11,439,837, issued Sep. 13, 2022, which is a divisional of U.S. patent application Ser. No. 16/938,275, filed Jul. 24, 2020, now U.S. Pat. No. 11,173,315, issued Nov. 16, 2021, which are incorporated by reference in their entireties.

BACKGROUND

Sudden cardiac arrest (e.g. heart failure) can involve the abrupt loss of heart function, breathing, and consciousness. In many cases, the condition can result from an electrical disturbance in the heart that disrupts its pumping action, which can stop blood flow within the body. In the United States alone, more than three hundred thousand people die from cardiac arrest outside hospitals every year.

SUMMARY

According to one aspect of the present disclosure, a mobile defibrillator system for use on a subject can include a device capable of running an application; and a mobile defibrillator (AED) unit configured to be connected to the device, the mobile AED unit comprising pads. The device, via the application, can be configured to detect when the mobile AED unit is connected to the device; analyze health data associated with the subject, the health data being stored on the application; determine that the pads have been attached to the subject; determine, based on the health data, an electrical shock pattern for administering to the subject; and administer the electrical shock pattern to the subject. In some embodiments, the determined electrical shock pattern can include a plurality of electrical shocks. Each electrical shock can include a duration and an energy level. The electrical shock pattern can further include a determined duration between electrical shocks.

In some embodiments, health data can include at least one of data associated with pulse rate frequency, pulse rate variations, heart rhythm, configuration of an EKG-complex, ST elevations, deprivations, cardiac ischemia, ventricular tachycardia, or ventricular fibrillation. In some embodiments, the device can be configured to, via the application, measure a current flowing between the pads; and based on the measured current, display a recommendation on the device for changing the distance between the pads. In some embodiments, determining, based on the health data, an electrical shock pattern for administering to the subject can include analyzing the health data with a machine learning model trained on historical defibrillator performance data and health data.

In some embodiments, the device can be configured to send performance and health data associated with AED performance to a server over a network. In some embodiments, the server can be configured to receive performance and health data from a plurality of user devices and a plurality of mobile AEDS and at least one of retrain or update the machine learning model based on the received performance and health data. In some embodiments, performance and health data can include at least one of data associated with pulse rate frequency, pulse rate variations, heart rhythm, configuration of an EKG-complex, ST elevations, deprivations, cardiac ischemia, ventricular tachycardia, ventricular fibrillation, a user interface, and user experience optimization.

According to another aspect of the present disclosure, a method for performing a self-rescue with a mobile defibrillator (AED) unit can include detecting, via an application on a user device, a connection of a mobile AED unit to the user device; detecting, via the application, that pads have been attached to a subject; recording, via the application, EKG measurements of the subject made by the pads; determining, based on the recorded EKG measurements and pre-programmed risk factors associated with the subject, an action to take using the mobile AED; and performing, via the application and the user device, the action on the subject. In some embodiments, the action can include at least one of administering an electrical shock pattern to the subject; continuing to record EKG measurements; and initiating a CPR protocol.

In some embodiments, the action can include administering an electrical shock pattern to the subject and the method can include determining, based on health data and the pre-programmed risk factors associated with the subject, an electrical shock pattern for administering to the subject. The electrical shock pattern can include a plurality of electrical shocks. Each electrical shock can include a duration and an energy level. The electrical shock pattern further can include a determined duration between electrical shocks. In some embodiments, the pre-programmed risk factors were received as user inputs into the application via a user interface on the user device.

In some embodiments, the method can include sending, via the device to a server over a network, performance and health data associated with AED performance. In some embodiments, the pads can include at least one accelerometer and determining the action can include receiving accelerometer data from the at least one accelerometer; analyzing the accelerometer data to determine a breathing pattern of the subject; and based on the determined breathing pattern, initiating the CPR protocol.

In some embodiments, the server can be configured to receive performance and health data from a plurality of user devices and a plurality of mobile AEDS and at least one of retrain or update a machine learning model for analyzing EKG measurements and a machine learning model for determining pad placement based on the received performance and health data. In some embodiments, determining that the action is administering an electrical shock pattern to the subject can include in response to detecting that the pads have been attached to the subject, displaying, via the application, notifications at a pre-defined frequency to the subject via the device; determining that the subject has not responded to at least one message within the time-period; and in response to determining that the subject has not responded, determining that the action is administering an electrical shock pattern to the subject. Each message can indicate a time-period for reply.

According to another aspect of the present disclosure, a method for performing CPR with a mobile defibrillator (AED) unit can include detecting, via an application on a user device, a connection of a mobile AED unit to the user device; detecting, via the application, that pads have been attached to a subject, the pads comprising at least one accelerometer; recording, via the application, EKG measurements of the subject made by the pads; receiving accelerometer data from the at least one accelerometer; analyzing the accelerometer data to determine a breathing pattern of the subject; and based on the determined breathing pattern, initiating a CPR protocol. In some embodiments, initiating the CPR protocol can include displaying instructions on the device to a user to provide CPR to the subject.

In some embodiments, the received accelerometer data can be first accelerometer data and the method can further include receiving second accelerometer data from the at least one accelerometer while CPR is being performed on the subject; analyzing the second accelerometer data to determine a frequency and force of pushing; and displaying a recommendation on the user device to change at least one of the frequency and the force of pushing. In some embodiments, the method can include determining, based on the health data and the EKG measurements, an electrical shock pattern for administering to the subject; and administering the electrical shock pattern to the subject in conjunction with the CPR protocol.

BRIEF DESCRIPTION OF THE DRAWINGS

The accompanying figures, where like reference numerals refer to identical or functionally similar elements throughout the separate views, together with the detailed description below, are incorporated in and form part of the specification, and serve to further illustrate embodiments of concepts that include the claimed invention and explain various principles and advantages of those embodiments.

Figure 1:
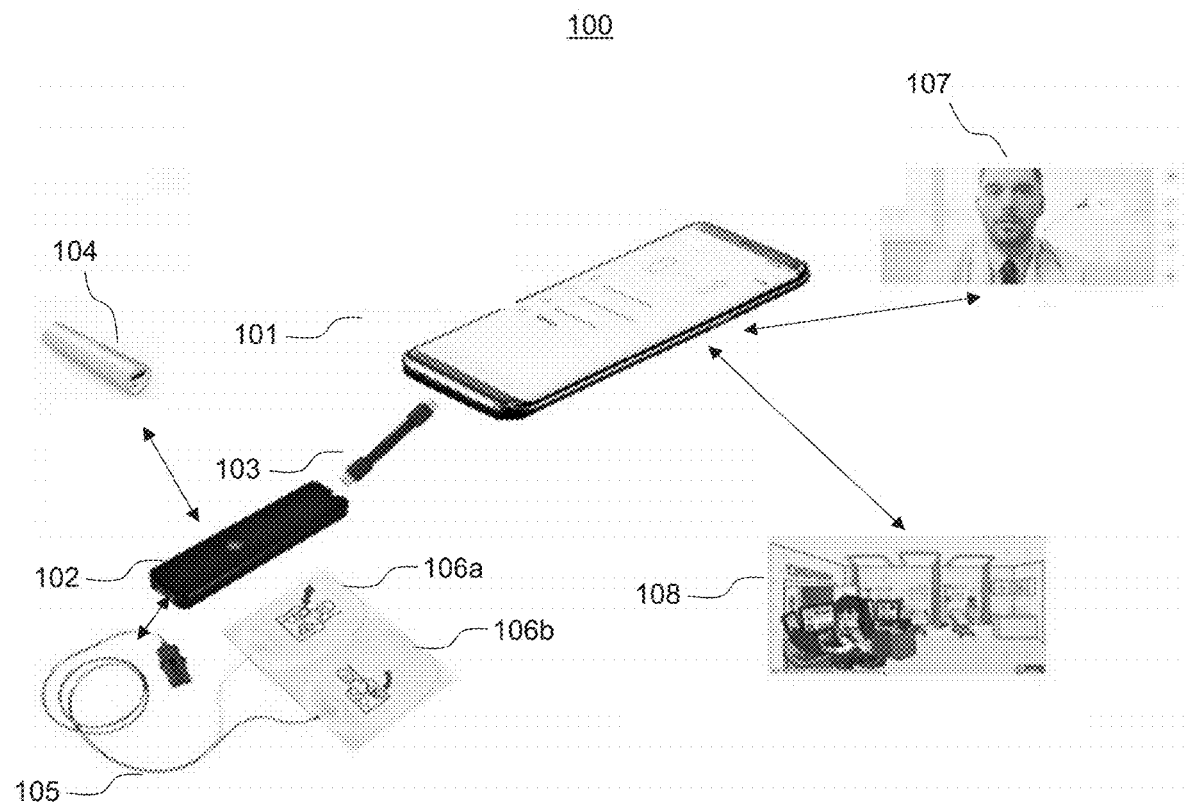
FIG. 1 is an example mobile automatic external defibrillator (AED) system, according to some embodiments of the present disclosure.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present disclosure.

The structural components of the security system have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

DETAILED DESCRIPTION

The availability of public defibrillators or automated external defibrillators (AEDs) can have a significant impact on survival for people that experience cardiac arrest. Cardiac arrest victims who receive an electrical shock from a publicly available AED have much higher survival rates. For every minute without cardiopulmonary resuscitation (CPR), the chance of death can increase by ten percent. However, AEDs are still not widely accessible by the public in a viable manner. Other challenges related to the widespread accessibility of AEDs are that many people in the "public" lack the necessary training to resuscitate and/or treat a cardiac arrest victim, the knowledge threshold to start CPR is too high, and current AED solutions can be expensive and bulky and can have a non-familiar user experience.

Accordingly, embodiments of the present disclosure relate to a mobile AED that can be controlled via an application on a device (e.g. smartphone, tablet, laptop, watches, car entertainment systems). In some embodiments, the mobile AED of the present disclosure can be carried around by a user (e.g. in a pocket or purse) and connected to a mobile device by plugging in a cord connector, such as a USB-C connection. In some embodiments, some of the operational logic of the AED can be offloaded to the mobile device and a user interface can be provided via the application that allows a user to control the AED; this can reduce the cost and threshold of use for such devices. The mobile AED described herein can utilize the existing battery, operating system (e.g. iOS, Android, etc.), speakers, voice assistant, video, GPS, WiFi, and/or mobile network connection of the device it is connected to. In some embodiments, the mobile AED can also include an additional port to facilitate connection to a power bank or other external power sources for charging and/or power.

The mobile AED of the present disclosure can be smaller and more widely available than any previous attempts. Any person that has access to devices that have microphones, speakers, data storage, and power sources can be used. The pads/electrodes that are used in conjunction with the mobile AED can include accelerometers and the defibrillator unit can include an electrical shock circuit. This can create a mobile AED that is easily carried around and more versatile. The mobile AED and application/device system can be configured to operate an algorithm that can analyze whether a subject has a heart rhythm that needs defibrillation, can automatically call for help (e.g. locally using a speaker/alarm or via the telephone network to emergency personnel), can guide local helpers in CPR and resuscitation by showing on the screen of the device what to do and giving instructions via the speaker, can find other mobile AEDs that are nearby, can generate strong enough voltages for effective electrical shocks, can generate repeated shocks, and can compile all data during processes and use the data to continuously learn new AED behaviors and improve the devices.

FIG. 1 is an example mobile AED 100, according to some embodiments of the present disclosure. Mobile AED 100 can include a defibrillator unit 102 removably connected via connection 103 to a device 101. Defibrillator unit 102 can include circuitry configured to generate specific pulses or shocks to administer to a patient for treating cardiac arrest victims (see FIG. 2). Note, while device 101 is a smartphone in this illustration of mobile AED 100, this is not limiting. Device 101 could be other devices with an operating system capable of running an application, such as a tablet, laptop, computer, watch, or car entertainment system. In some embodiments, connection 103 can include a USB-C connection or other similar connections. Connection 103, when connecting device 101 and defibrillator unit 102, can allow for defibrillator unit 102 to be controlled via a user interface and application on device 101. In some embodiments, defibrillator unit 102 can optionally include an additional connection port to power bank 104 (e.g. portable charger, outlet, etc.), which can also be a USB-C port, but may be different than the port for connection 103.

Defibrillator unit 102 can include an additional port for connection to a wire 105; wire 105 can act as a medium for which shocks determined and/or generated by circuitry within defibrillator 102 can be transferred to pads 106*a-b*. Pads 106*a-b* can be any standard defibrillator pads known in the art and can be configured to stick to a patient's body and operate as electrodes to feed current into a person's body from the defibrillator unit 102. In some embodiments, pads 106*a-b* can also include accelerometers. In some embodiments, when defibrillator unit 102 is connected or plugged into device 101, a user can connect to a video assistant specialist 107. In some embodiments, a team of specialists can work on call and can communicate with a user of the device. For example, if someone suddenly experiences cardiac arrest, a nearby person could connect the defibrillator unit 102 to device 101, navigate to the application (or the application can open automatically in response to connection), and select an option to immediately join a video session with a specialist, who can help the person administer a shock and/or CPR to the victim. In some embodiments, a person can also, via the application on device 101, connect to emergency services (e.g. call 911). In some embodiments, the application on the device 101 can be configured to be controlled remotely by emergency personnel or a mobile AED specialist. This can allow for, since the defibrillator unit 102 is controlled by the application on the device 101, emergency personnel to actually control and implement electrical shocks to a subject connected to the defibrillator unit 102. In some embodiments, defibrillator unit 102 can be configured to receive power from 220 V power sources or sockets or from 12 V sockets in a vehicle.

In some embodiments, the application on the device 101 can also be configured to receive data from external devices connected to user device 101, such as a smartwatch or other similar device that monitors the subject. For example, a person's smartwatch may consistently monitor their heartbeat and transmit this information to user device 101. Application 304 can be configured to monitor and analyze the subject's heartbeat and potentially identify and/or detect dangerous rhythms (e.g. rapid ventricular tachycardia, ventricular fibrillation, or other rhythm indicators that a neural network has been trained to detect). In response to detecting a dangerous rhythm, the application can be configured to notify the subject via device 101 and instruct them to connect their mobile AED and pads and potentially begin a self-rescue protocol.

Figure 2:
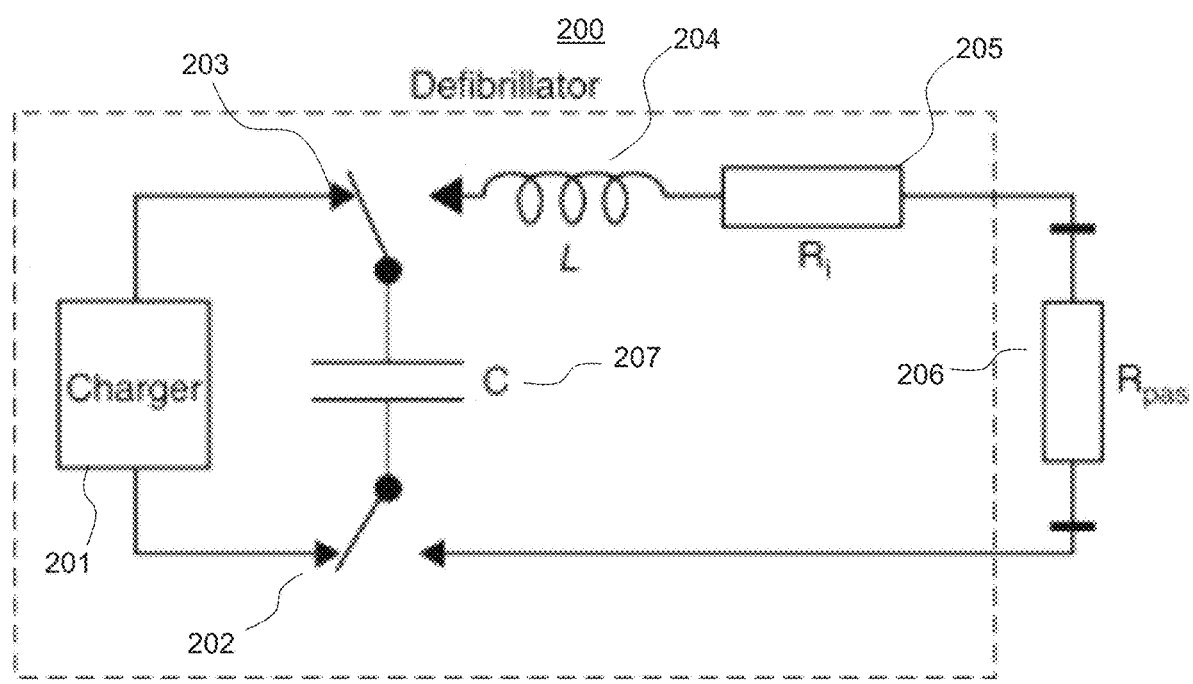
FIG. 2 is an example circuit schematic of a mobile AED, according to some embodiments of the present disclosure.

FIG. 2 is an example circuit schematic 200 of a mobile AED, according to some embodiments of the present disclosure. Circuit 200 can be included within the defibrillator unit 102 of FIG. 1. In some embodiments, circuit 200 can include a charger 201, switches 202 and 203, an inductor 204, resistor 205, pass resistance 206, and capacitor 207. In some embodiments, pass resistance 206 can represent the resistance within a person's body that exists between pads 106*a* and 106*b* while they are connected. When switches 202 and 203 are in a leftward position (as shown in FIG. 2), charger 201 can charge the capacitor 207. In some embodiments, charger 201 can represent the battery of a connected device (e.g. device 101 of FIG. 1), an external power bank (e.g. power bank 104 of FIG. 1), or a combination of both. Switches 202 and 203 can be controlled via logic within device 101 and via the application that a user can navigate on the device 101. For example, the application can determine a time in which a shock (e.g. pulse of current/energy) should be administered to the patient, and, in order to administer the shock, the switches 202 and 203 move to the rightward position (not shown in FIG. 2), which can allow current to flow from capacitor 207 through the patient, inductor 204, and resistor 205. The current, when flowing through the patient's heart, can serve to resuscitate the subject until paramedics or other emergency response teams can stabilize the subject. In some embodiments, the circuit 200 can be configured to provide pulses of up to 200 J repeatedly for up to one hour.

Figure 3:
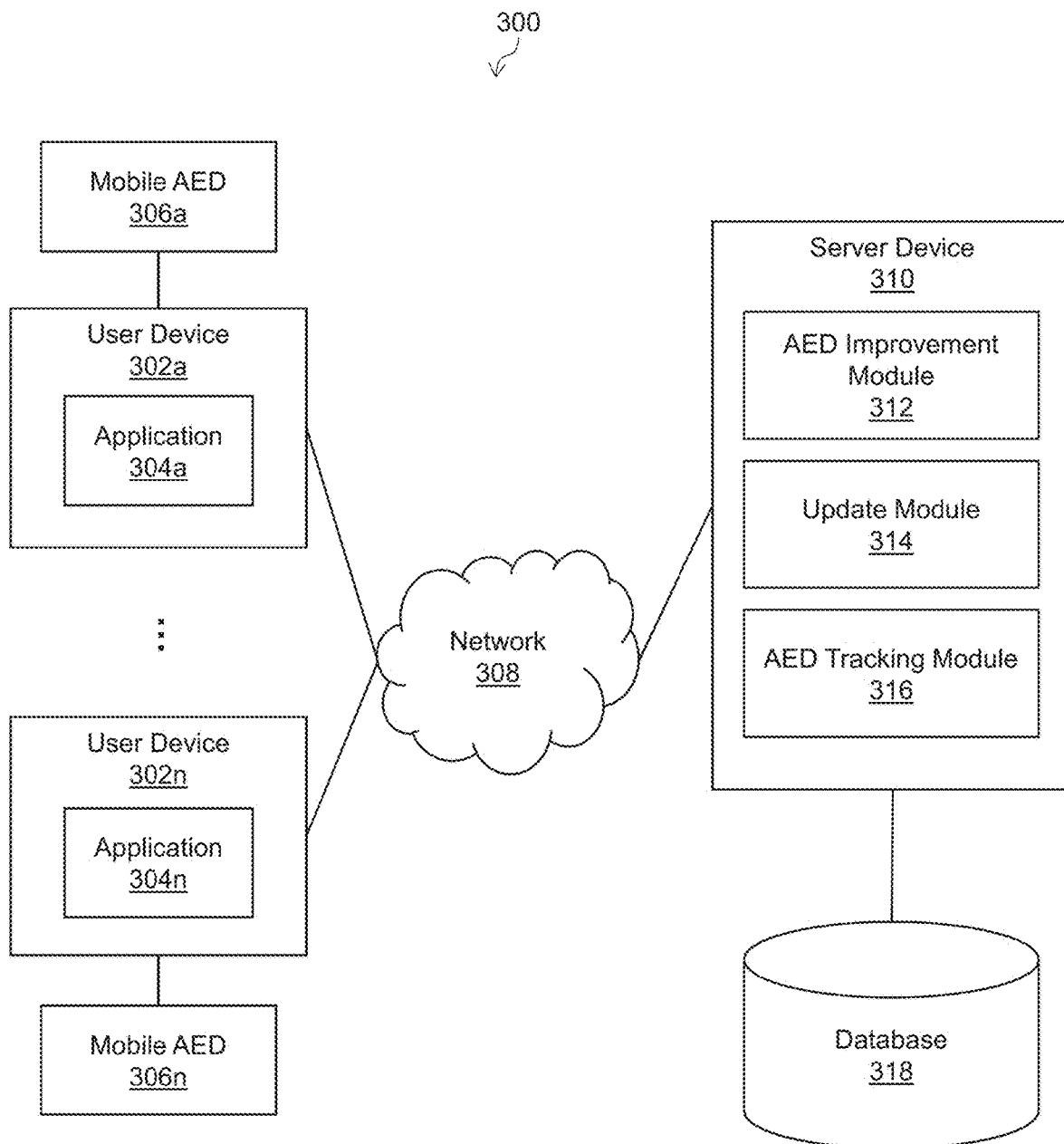
FIG. 3 is a block diagram of a system of mobile AED devices, according to some embodiments of the present disclosure.

FIG. 3 is a block diagram of a system 300 of mobile AED devices, according to some embodiments of the present disclosure. In some embodiments, system 300 can include a plurality of user devices 302*a-n* (user device 302 generally) communicably coupled to server device 310 via network 308. Note, system 300 includes two user devices 302*a-n* for illustrative purposes but any number of user devices can be included within the system of the present disclosure.

In some embodiments, network 308 may include one or more wide areas networks (WANs), metropolitan area networks (MANs), local area networks (LANs), personal area networks (PANs), or any combination of these networks. Network 308 may include a combination of one or more types of networks, such as Internet, intranet, Ethernet, twisted-pair, coaxial cable, fiber optic, cellular, satellite, IEEE 801.11, terrestrial, and/or other types of wired or wireless networks. Network 308 can also use standard communication technologies and/or protocols.

In some embodiments, a user device 302 can be similar to or the same as device 101 of FIG. 1. For example, user device 302 can include a smartphone, tablet, laptop, watch, car entertainment system, or a combination of similar types of devices that can run a software application and utilize an operating system. A user device 302 can include one or more computing devices capable of receiving user input as well as transmitting and/or receiving data via network 308 or communicating with server device 310. In some embodiments, user device 302 can include a conventional computer system, such as a desktop or laptop computer. Alternatively, user device 302 can include a device having computer functionality, such as a personal digital assistant (PDA) or other suitable device. Additionally, each user device 302 can include a specifically installed application 304 for use in conjunction with a connected mobile AED 306. Application 304 can include software instructions, which can be stored on a non-transitory computer readable medium, that, when executed by a processor (e.g. a processor within user device 302), can perform various processes related to administering shocks as an AED and reading EKGs in conjunction with a mobile AED 306. Note additional detail related to AED processing will be described in relation to FIGS. 4-7.

Server device 310 may include any combination of one or more of web servers, mainframe computers, general-purpose computers, personal computers, or other types of computing devices. Server device 310 may represent distributed servers that are remotely located and communicate over a communications network, or over a dedicated network such as a local area network (LAN). Server device 310 may also include one or more back-end servers for carrying out one or more aspects of the present disclosure. In some embodiments, server device 108 may be the same as or similar to server device 700 described below in the context of FIG. 7.

As shown in FIG. 3, server device 310 can include an AED improvement module 312, an update module 314, and an AED tracking module 316. Additionally, server device 310 can be communicably coupled to a database 318. In some embodiments, AED improvement module 312 can include one or more models/algorithms trained via machine learning that can be used to continuously improve AED and/or CPR performance overtime. In some embodiments, AED improvement module 312 can be configured to continuously receive performance data from user devices 302 and retrain or update models to reflect newly received performance data. In some embodiments, AED improvement module 312 can also have access to Emergency Health Records and other external databases to obtain additional training data. In some embodiments, AED improvement module 312 can be configured to analyze, retrain, and/or update various machine learning models related to AED performance, such as models that determine lengths and levels of initial pulses, pad placement, body part detection, how often to provide additional pulses, the amount of energy in each pulse, and various other decisions related to electrocardiogram (EKG) readings, which will be described in additional detail in relation to FIGS. 4-7.

In some embodiments, update module 314 can be configured to package or incorporate updated/retrained models from AED improvement module 312 into a software update and distribute the update to the user devices 302. In some embodiments, the update may be received by user device 302 via download from an application store. In addition, AED tracking module 316 can be configured to track locations of each mobile AED 306. In some embodiments, AED tracking module 316 can utilize GPS coordinates obtained from user device 302. In some embodiments, AED tracking module 316 can allow for a user to, via the application 304 on a user device 302, search for nearby mobile AEDs 306.

The various system components—such as modules 312-316 and 304a-n—may be implemented using hardware and/or software configured to perform and execute the processes, steps, or other functionality in conjunction therewith.

Figure 4:
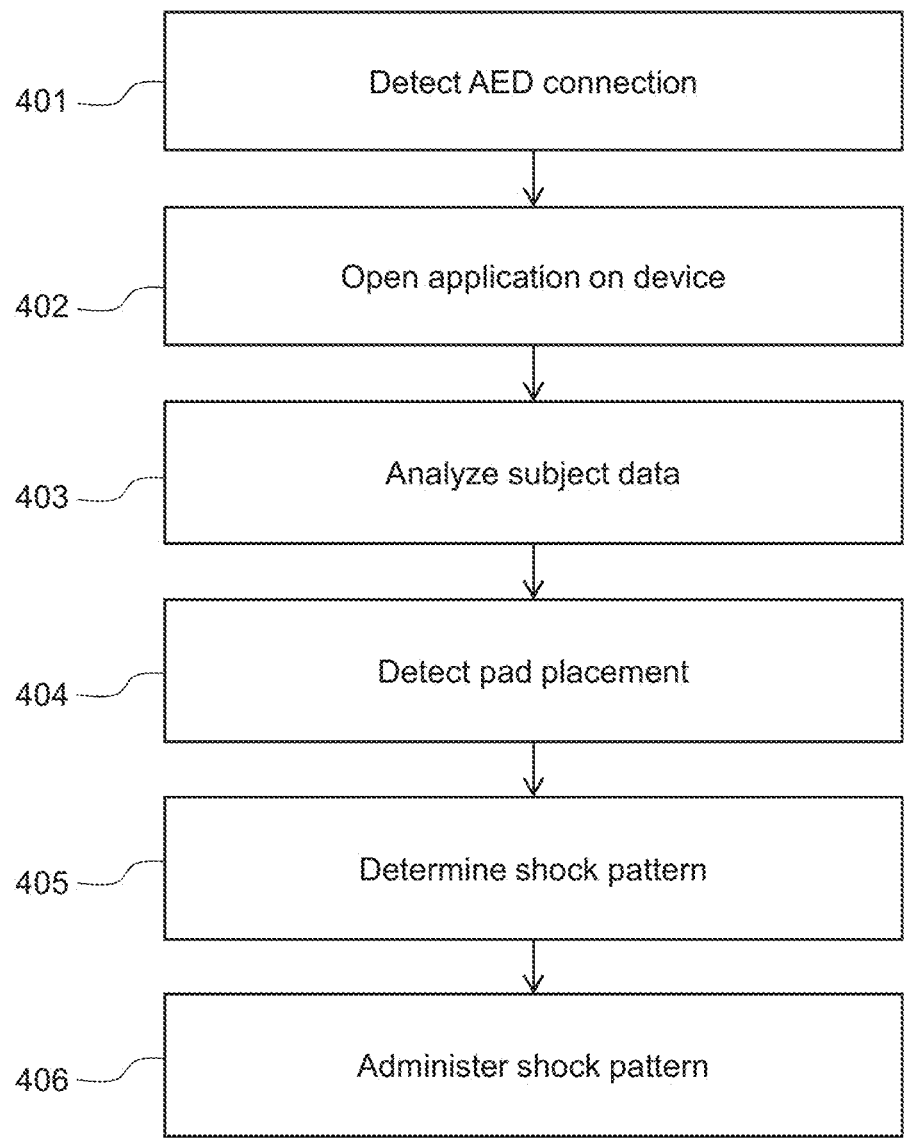
FIG. 4 is an example process for using a mobile AED, according to some embodiments of the present disclosure.

FIG. 4 is an example process 400 for using a mobile AED, according to some embodiments of the present disclosure. In some embodiments, process 400 can be performed by a user device (e.g. user device 302 and/or user device 101). In some embodiments, performance of process 400 can be assisted by a user interacting with the user device. For example, in response to a person experiencing sudden cardiac arrest, a bystander or friend or other individual may utilize a mobile AED of the present disclosure and an application (e.g. application 304) on a user device to perform process 400. At block 401, user device 302 (e.g. via application 304) can detect an AED connection. For example, the user can locate a mobile AED (e.g. defibrillator unit 102) and connect the defibrillator unit 102 to the user device, such as by plugging in a connection cable. The user device, for example via application 304, can detect that the defibrillator unit 102 has been connected. At block 402, user device 302 can open an application 304. In some embodiments, the application 304 can be automatically opened in response to detection of the defibrillator connection; in some embodiments, the application may be opened manually by the user.

At block 403, the application 304 can analyze data associated with the subject (e.g. the person who has recently gone into cardiac arrest). For example, the application 304 may store demographic and health information associated with the subject by previously allowing the subject access to input self-describing information. The application 304 can store various types of information such as height, weight, age, blood pressure, previous EKG ratings, medical history, etc. In some embodiments, application 304 can be configured to utilize a machine learning algorithm to analyze the subject information to make various determinations related to the remaining steps for administering AED treatment. In some embodiments, the analysis can be performed external from the user device 302; for example, the subject data may be sent and processed by a server (e.g. server 310), and the results of the processing may be transmitted to the user device 302 to affect treatment.

At block 404, application 304 can detect a pad placement. In some embodiments, the application 304 can be configured to, based on electrical measurements (e.g. current) from the pads 106a-b, detect whether a human body is connected between the two pads. In some embodiments, detecting the pad placement can include, once the pads (e.g. pads 106a-b) are placed on a subject's body (e.g. under the subject's right collarbone and below the subject's left armpit), application 304 can detect the amount of current flowing through the subject and between the pads. Based on the strength of the detected current, application 304 can determine whether the pads are too far apart or too close together. For example, application 304 can utilize a threshold current range and compare the detected current to the threshold. If the detected current is above or below the threshold, application 304 can display a warning on the device to the user that recommends moving the pads closer or farther away from each other.

At block 405, application 304 can be configured to determine a shock pattern to administer to the subject. In some embodiments, determining the shock pattern can include application 304 utilizing a machine learning model to analyze data associated with the subject (e.g. height, weight, pad placement, EKG measurements, etc.) and output a shock pattern to resuscitate the subject. In some embodiments, application 304 can obtain and analyze data (e.g. operate as an EKG machine) via the connected pads prior to determining a shock pattern and use the obtained data to determine the shock pattern. For example, the machine learning model can be trained to determine the shock pattern based on data such as pulse rate (both frequency and variations), all types of heart rhythm, the configuration of the EKG-complexes, ST elevations (e.g. the vertical distance inside the EKG trace and the baseline), deprivations, and signs of cardiac ischemia, ventricular tachycardia, and ventricular fibrillation. Application 304 can also be configured to detect that certain breathing patterns occurring in association with ventricular extrasystoles can be a trigger event. In some embodiments, the machine learning model can include a neural network with a plurality of nodes trained to map the aforementioned types of health data to various factors in shock patterns (e.g. durations, timing, and energy levels). In some embodiments, application 304 can be configured to estimate a subject's fat percentage based on electrical measurements received from the pads 106a-b, and the fat percentage can be used in determining the electrical shock pattern. In some embodiments, the machine learning model can also be configured to predict if subjects will get "return of spontaneous circulation" (ROCS), which can include the resumption of sustained perfusing cardiac activity. This can be predicted by analyzing breathing, movement, pulse, and blood pressure.

In some embodiments, the shock pattern can include a duration and level (e.g. energy level in Joules) of a plurality of energy pulses. In some embodiments, the initial pulse to a subject experiencing cardiac arrest can be important with regard to resuscitation. At block 406, application 304 can cause defibrillator unit 102 to administer the determined shock pattern to the subject. Administering the shock pattern can include utilizing the power source of user device 302 to power the circuitry (e.g. circuit 200) within the defibrillator unit 102. A possible benefit of utilizing the power circuitry within a mobile device is that it can provide for a cheaper device, which can ultimately be more accessible for more people and increase the prevalence of its use. In some embodiments, application 304 can be configured to give a warning to people nearby before the electrical shock pattern is administered. For example, application 304 can utilize speakers and the user interface of the device 101 to sound off and display a warning to move away from the person while the electrical shock is being administered. This can prevent current from shocking or harming other people. In some embodiments, after the electrical shock pattern has completed, application 304 can display and sound another message indicating an all-clear.

In some embodiments, prior to determining the shock pattern at block 406, the mobile AED can be configured to operate as an EKG for a period of time. The application can be configured to receive the data and EKG measurements and make various determinations related to the shock pattern based on these measurements. In some embodiments, upon completion of any shock pattern administered, all data/information associated with the process can be sent from user device 302 to server 310, specifically to AED improvement module 312. AED improvement module 312 can utilize the received information to update and/or retrain any machine learning models related to determining shock patterns and pad placement based on both demographic and health data and EKG measurements. In some embodiments, a large plurality of mobile AEDs could be utilized, thus providing large and rich datasets for which to continuously update algorithms and models related to the AED performance. Because of the nature of operation of the present disclosure (utilizing an application interface in a standard operating system to administer an AED), this can allow for AED performance to be continuously updated and improved upon.

In some embodiments, process 400 can be performed in accordance with a video assistant and/or voice assistant. For example, application 304 can be configured to utilize any voice assistant functionality on the device (e.g. Alexa, Google Assistant, Siri, voice systems in vehicles, etc.). For example, if a person opens the app but does not know how to administer the AED to a victim, the person could communicate with the application 304 via voice assistant and ask for help. In some embodiments, the application can connect to a specialist via video and can activate a camera on the mobile device 302. In some embodiments, a team of specialists can be assembled that can handle the inflow of video connections. Each specialist can be equipped with the knowledge of how to operate a mobile AED 306 which can provide quick and effective assistance in the case of an emergency, as well as reliable information. This can be more beneficial than the ability to connect to a doctor or similar figure as there is no issue of availability. In some embodiments, the application 304 can also allow a user to connect immediately to law enforcement and/or emergency personnel. In some embodiments, in response to notifying law enforcement or emergency personnel through the application 304, GPS and medical data associated with the subject can be immediately forwarded to law enforcement via the application 304. This can provide valuable information to emergency personnel beforehand which can save potentially precious time once the personnel have arrived on scene.

In some embodiments, the application 304 can also assist with performing CPR in accordance with administering a shock pattern. In some embodiments, the application 304 can be configured to detect the strength of pushing that an individual is providing to a subject's chest cavity by analyzing the forces on the pads 106a-b. The application 304 can provide indications to the user such as "push harder" or "push softer." Additional details with regards to CPR are described in relation to FIG. 5.

Figure 5:
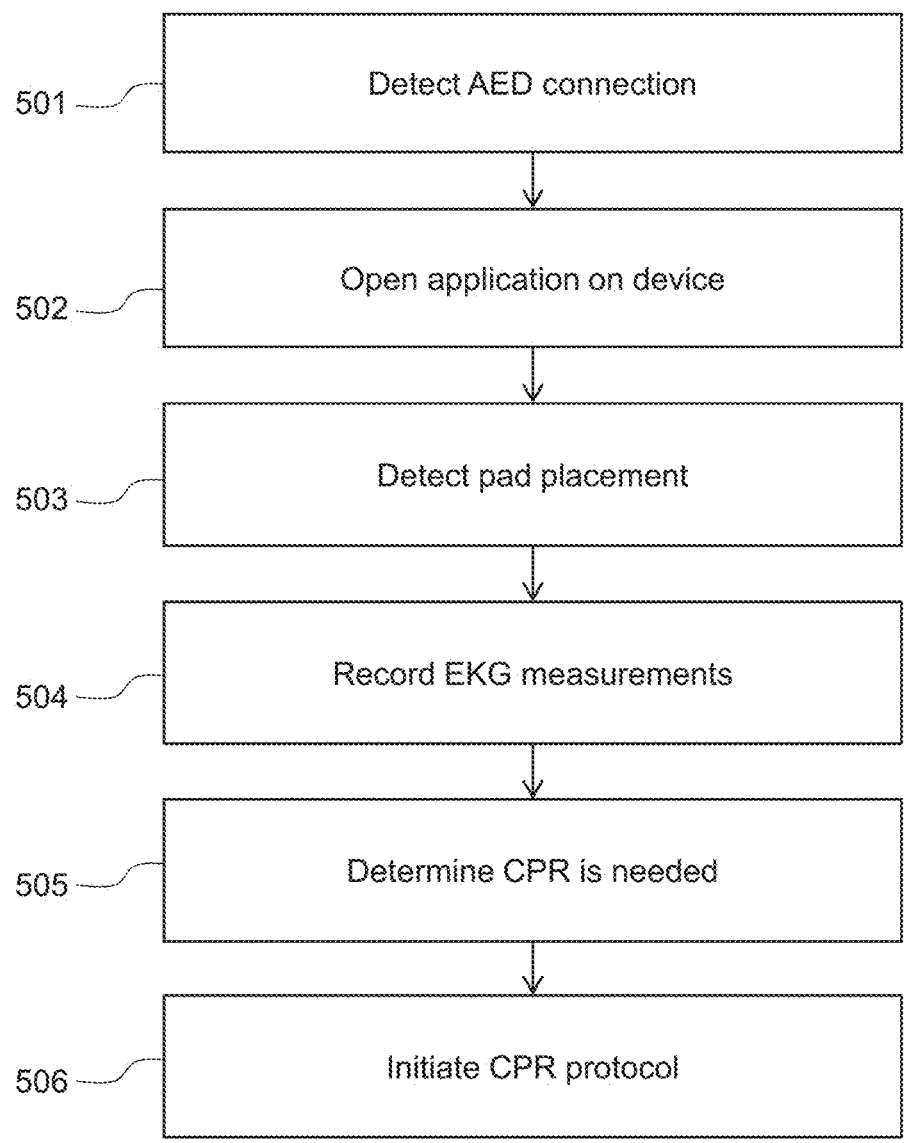
FIG. 5 is an example processing for assisting with CPR with a mobile AED, according to some embodiments of the present disclosure.

FIG. 5 is an example process 500 for assisting with CPR with a mobile AED, according to some embodiments of the present disclosure. In some embodiments, process 500 can be performed by application 304 on a device 101. Additionally, in some embodiments, process 500 can be performed in conjunction (e.g. simultaneously or consecutively with) with process 400. In some embodiments, performance of process 500 can be assisted by a user interacting with the user device. For example, in response to a person experiencing sudden cardiac arrest, a bystander or friend or other individual may utilize a mobile AED of the present disclosure and an application (e.g. application 304) on a user device to perform process 500. At block 501, user device 302 (e.g. via application 304) can detect an AED connection. For example, the user can locate a mobile AED (e.g. defibrillator unit 102) and connect the defibrillator unit 102 to the user device, such as by plugging in a connection cable. The user device, for example via application 304, can detect that the defibrillator unit 102 has been connected. At block 502, user device 302 can open an application 304. In some embodiments, the application 304 can be automatically opened in response to detection of the defibrillator connection; in some embodiments, the application may be opened manually by the user.

At block 503, application 304 can detect a pad placement. In some embodiments, the application 304 can be configured to, based on electrical measurements (e.g. current) from the pads 106a-b, detect whether a human body is connected between the two pads. In some embodiments, detecting the pad placement can include, once the pads (e.g. pads 106a-b) are placed on a subject's body (e.g. under the subject's right collarbone and below the subject's left armpit), application 304 can detect the amount of current flowing through the subject and between the pads. Based on the strength of the detected current, application 304 can determine whether the pads are too far apart or too close together. For example, application 304 can utilize a threshold current range and compare the detected current to the threshold. If the detected current is above or below the threshold, application 304 can display a warning on the device to the user that recommends moving the pads closer or farther away from each other.

At block 504, now that the pads 106a-b are connected to the individual's body, the pads 106a-b can operate as electrodes and application 304 can record EKG measurements of the person's heart behavior. In some embodiments, recording EKG measurements can include sensing electrical activity of the subject's heart while the pads are attached. The electrical activity can be detected and sent to the application 304 for various analytical purposes. The application 304 can be configured to monitor and analyze the EKG measurements and detect irregularities/anomalies or any disturbances or factors that may suggest a heart attack or cardiac arrest is likely to occur. The analysis can be performed via a machine learning model trained on substantial amounts of patient data that has been obtained from emergency health records, as well as real-time data from other mobile AEDs 306 connected to server device 310. In some embodiments, application 304 can obtain and analyze data (e.g. operate as an EKG machine) via the connected pads, such as pulse rate (both frequency and variations), all types of heart rhythm, the configuration of the EKG-complexes, ST elevations (e.g. the vertical distance inside the EKG trace and the baseline), deprivations, and signs of cardiac ischemia, ventricular tachycardia, and ventricular fibrillation.

At block 505, application 304 can determine that CPR is needed to resuscitate the patient. In some embodiments, determining that CPR is needed can include detecting a heart rhythm via the recorded EKG measurements that can indicate a lack of blood circulation, such as ventricular tachycardia and/or ventricular fibrillation. In some embodiments, determining that CPR is needed can include detecting non-normal breathing. In some embodiments, application 304 can be configured to, once the pads have been placed on the subject, receive accelerometer data from the pads 106a-b. Application 304 can be configured to use the accelerometer data to map, analyze, and estimate breathing patterns. For example, application 304 can use the accelerometer data to model chest movements and analyze the frequency of breathing; if the movement frequency is substantially different than around ten to twenty breaths per minute, this can be considered a non-normal breathing pattern and can suggest that CPR is needed. At block 506, application 304 can initiate a CPR protocol. In some embodiments, CPR protocol can include videos, instructions, or connections to a video specialist to guide a user on providing CPR to the subject. Instructions can be shown on the screen of the user device and/or via spoken voice assistant on the device. In some embodiments, when process 500 is performed in conjunction with administering an electrical shock pattern to the subject (such as described in FIG. 4), application 304 can provide warnings immediately before and during the electrical shock, and then indicate to the user that it is safe to perform chest compressions. In some embodiments, application 304 can be configured to receive accelerometer data from the pads 106a-b while CPR is being performed. Application 304 can be configured to analyze the accelerometer data to detect a rhythm at which cardiac compressions are being performed and can provide feedback to the user on both frequency and force. For example, the cardiac compressions may be given with too high or too low of a frequency (e.g. below 100 Hz or above 120 Hz) or the cardiac compressions may not be forceful enough. In some embodiments, initiating a CPR protocol can also include an immediate notification to law enforcement and/or emergency personnel.

Figure 6:
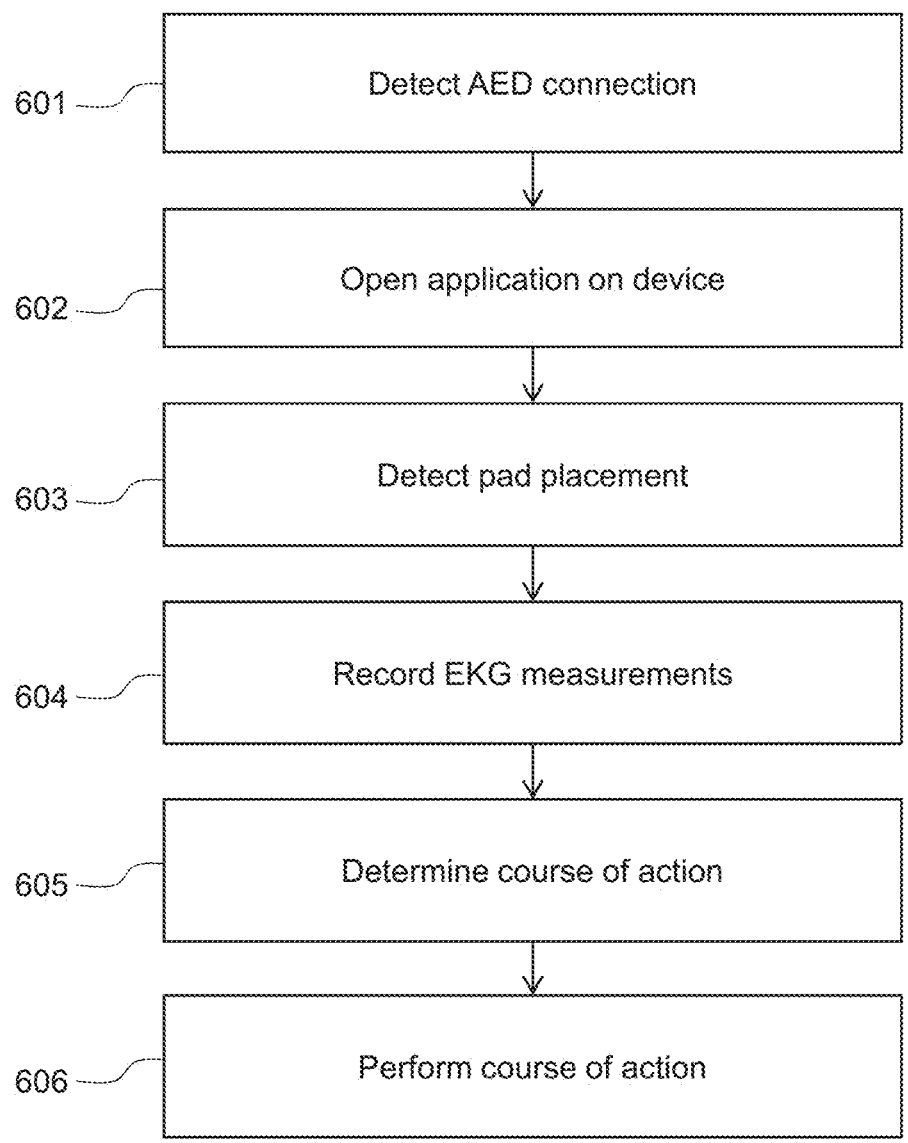
FIG. 6 is an example process for self-rescue with a mobile AED, according to some embodiments of the present disclosure.

FIG. 6 is an example process 600 for self-rescue with a mobile AED, according to some embodiments of the present disclosure. In some embodiments, process 600 can be performed by a person on themselves and can be referred to as a "self-rescue" operation. In some embodiments, a mobile AED of the present disclosure can be small, light, and convenient enough for a person to carry around easily in a purse, bag, or pocket as a potentially life-saving device. However, the mobile AED of the present disclosure can, in self-rescue applications, also be used by a person at the onset or very early stages of ill-feeling related to heart conditions. As opposed to process 400, which can be used to resuscitate a person undergoing heart failure or cardiac arrest who most normally be incapacitated to an extent, process 600 can be used by an individual on themselves. For example, if a person were to begin to feel symptoms of potentially oncoming cardiac arrest (e.g. tingling, heart flutter, etc.), that person could use a device (e.g. use device 302) to perform process 600 and potentially save themselves.

In response to noticing any feelings of concern, a user can connect his or her mobile AED 306 to their device 302. At block 601, user device 302 (e.g. via application 304) can detect an AED connection. For example, the user can locate a mobile AED (e.g. defibrillator unit 102) and connect the defibrillator unit 102 to the user device, such as by plugging in a connection cable. The user device, for example via application 304, can detect that the defibrillator unit 102 has been connected. At block 602, user device 302 can open an application 304. In some embodiments, the application 304 can be automatically opened in response to detection of the defibrillator connection; in some embodiments, the application may be opened manually by the user.

At block 603, in response to the individual sticking the pads (e.g. pads 106a-b) to themselves (for example on both of their pectoral muscles, surrounding the heart, etc.), the application 304 can detect the pad placement. For example, the application 304 can be configured to, based on electrical measurements from the pads 106a-b, detect whether a human body is connected between the two pads. At block 604, now that the pads 106a-b are connected to the individual's body, the pads 106a-b can operate as electrodes and application 304 can record EKG measurements of the person's heart behavior. In some embodiments, recording EKG measurements can include sensing electrical activity of the subject's heart while the pads are attached. The electrical activity can be detected and sent to the application 304 for various analytical purposes. The application 304 can be configured to monitor and analyze the EKG measurements and detect irregularities/anomalies or any disturbances or factors that may suggest a heart attack or cardiac arrest is likely to occur. The analysis can be performed via a machine learning model trained on substantial amounts of patient data that has been obtained from emergency health records, as well as real-time data from other mobile AEDs 306 connected to server device 310. Accordingly, at block 605, application 304 can determine a course of action based on the recorded EKG measurements and resulting analysis, as well as pre-specified or pre-programmed risk factors associated with the patient. For example, the patient can submit various information and risk factors within the application 304. For example, application 304 can administer a certain shock pattern with a certain timing or continuing to monitor the person's heart behavior. In some embodiment, administering a shock pattern can be caused by detecting a shockable heart rhythm from the EKG measurements (e.g. ventricular tachycardia and/or ventricular fibrillation). In some embodiments, detecting a non-normal breathing pattern (such as described in relation to FIG. 5) can suggest that administering an electrical shock is preferred. In some embodiments, application 304 can be configured to determine if a patient is unconscious. For example, after the pads have been connected to the subject, application 304 can display a message to the subject and ask that the subject respond in a certain way (e.g. pressing a button "yes I'm conscious" or responding verbally). If the subject does not respond within a pre-defined timeframe, application 304 can determine that the subject is unconscious and that an electrical shock is required. At block 606, the application 304 can perform the determined course of action.

Figure 7:
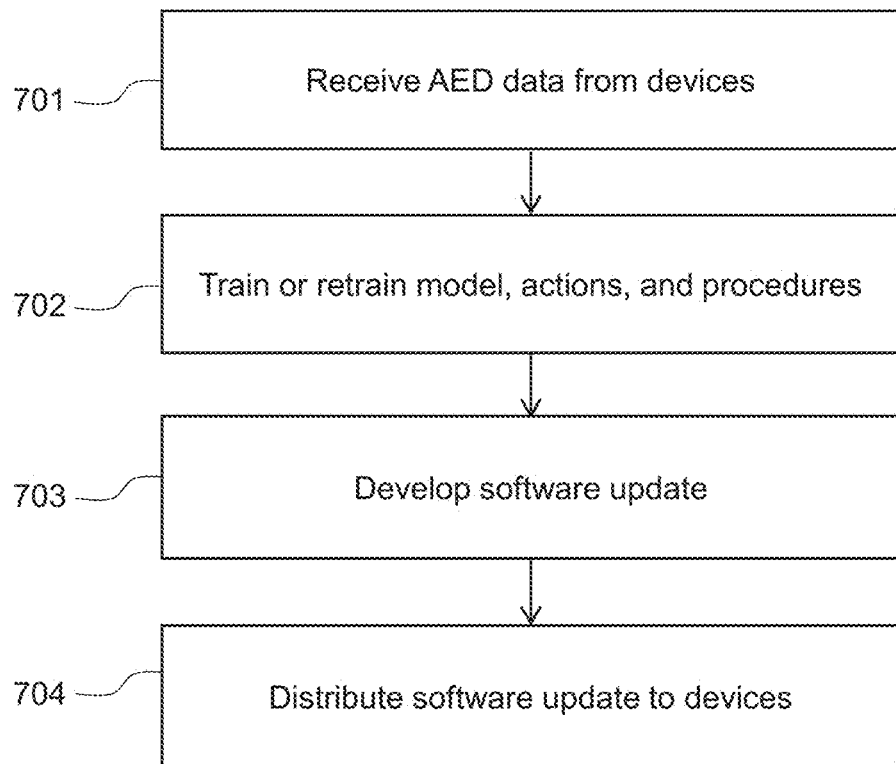
FIG. 7 is an example process for providing updates to a plurality of mobile AEDs, according to some embodiments of the present disclosure.

FIG. 7 is an example process 700 for providing updates to a plurality of mobile AEDs, according to some embodiments of the present disclosure. In some embodiments, process 700 can be performed by AED improvement module 312 and AED update module 314 to continuously, and sometimes in real-time, maintain and update various machine learning algorithms associated with AED performance for a mobile AED of the present disclosure. At block 701, AED improvement module can be configured to receive AED data from a plurality of devices (e.g. plurality of user devices 302). In some embodiments, AED data can include EKG measurements, health and demographic data of a patient, EKG measurements and other heart-monitoring related data recorded during processes performed on an individual (e.g. processes 400, 500, and 600). For example, the data may be compiled by application 304 and transmitted over network 308 to server device 310 and ultimately to AED improvement module 312. In some embodiments, application 304 can be configured to anonymize the information before transmitting it to the server device 310. Additionally, in some embodiments, AED improvement module 312 can also be configured to receive user interface data and user experience optimization data, which can be used to continuously improve application performance along with AED performance. The data received by AED improvement module 312 can include data from a plurality of mobile AEDs and from actual CPR and AED usage; this can include health and medical results and data (e.g. EKG measurements and other health data as described elsewhere in the specification), timing data (e.g. time to detect, time to get the AED ready, time to first shock, etc.), user interface data, user interaction data, data on the dependence on the number of people and who is present if possible, and location data.

At block 702, AED improvement module 312 can train or retrain models, actions, and procedures. For example, AED improvement module 312 can utilize the data receive from user devices 302 that operate in conjunction with mobile AEDs 306 to update or retrain various models maintained in server 310 (note the models also operate within application 304 on each user device 302). In some embodiments, AED improvement module 312 can be configured to utilize certain subsets of the data as training data and other subsets of the data as test data. The AED improvement module 312 can use the data to update models related to determining pad placement, determining shock patterns (e.g. duration and level of pulse), analyzing EKG measurements, and determining actions/procedures to take in response to monitoring an individual's EKG measurements during a self-rescue procedure.

At block 703, the update module 314 can compile all updated models and algorithms into a software update and provide the update either directly to user devices 302 or for download via an application store. In some embodiments, blocks 701 and 702 can be performed continuously and real-time; in other words, the various models used for mobile defibrillation can be continuously updated and trained. However, block 703 may only be performed at various stages or after certain levels of performance increases have been detected by AED improvement module 312. At block 704, the software update can be distributed to devices 302 to run on application 304.

Figure 8:
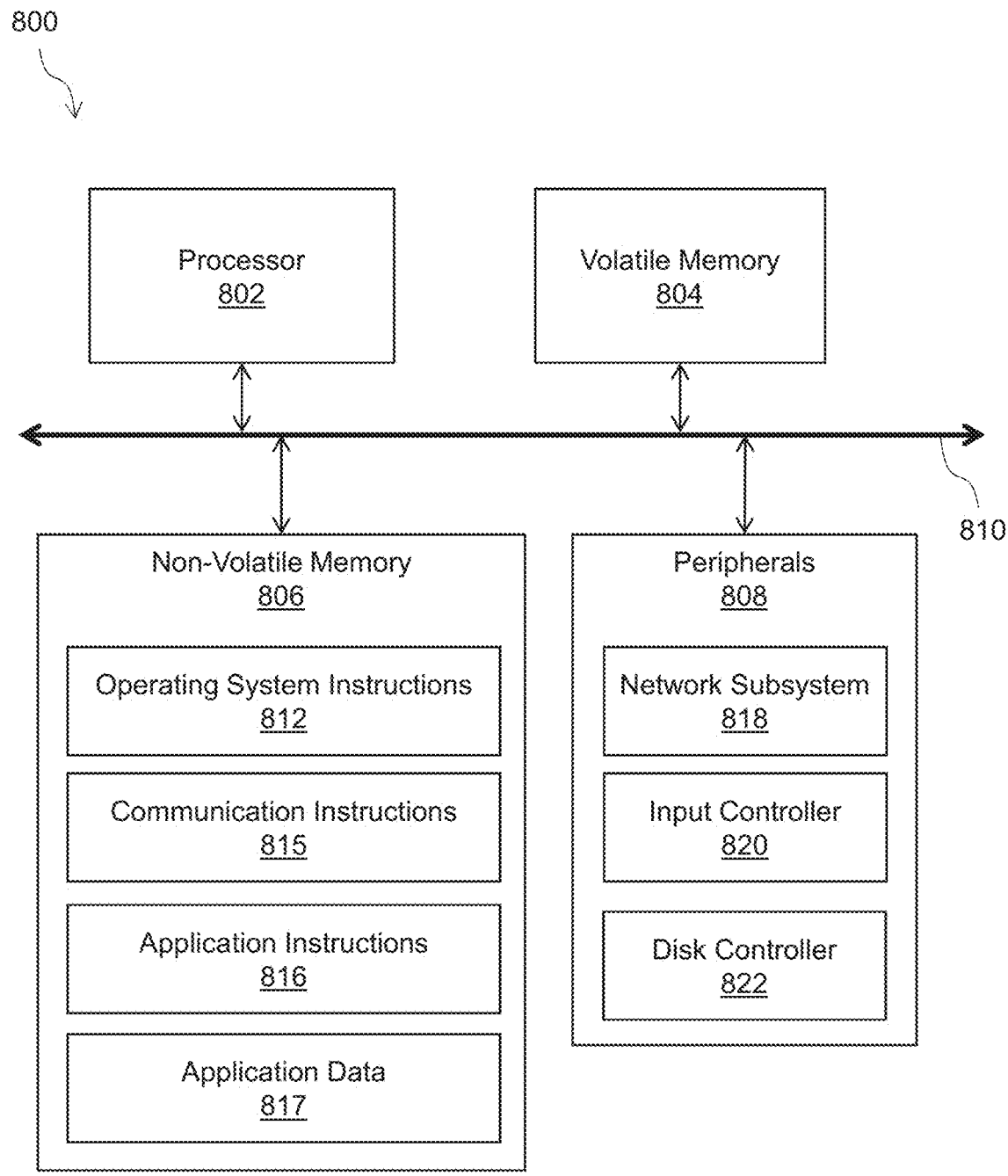
FIG. 8 is an example computing device that can be used within the system of FIGS. 1 and/or 3, according to some embodiments of the present disclosure.

FIG. 8 is an example server device 800 that can be used within the system of FIG. 3, according to some embodiments of the present disclosure. Server device 800 may implement various features and processes as described herein. Server device 800 may be implemented on any electronic device that runs software applications derived from complied instructions, including without limitation personal computers, servers, smart phones, media players, electronic tablets, game consoles, email devices, etc. In some implementations, server device 800 may include one or more processors 802, volatile memory 804, non-volatile memory 806, and one or more peripherals 808. These components may be interconnected by one or more computer buses 810.

Processor(s) 802 may use any known processor technology, including but not limited to graphics processors and multi-core processors. Suitable processors for the execution of a program of instructions may include, by way of example, both general and special purpose microprocessors, and the sole processor or one of multiple processors or cores, of any kind of computer. Bus 810 may be any known internal or external bus technology, including but not limited to ISA, EISA, PCI, PCI Express, NuBus, USB, Serial ATA, or FireWire. Volatile memory 804 may include, for example, SDRAM. Processor 802 may receive instructions and data from a read-only memory or a random access memory or both. Essential elements of a computer may include a processor for executing instructions and one or more memories for storing instructions and data.

Non-volatile memory 806 may include by way of example semiconductor memory devices, such as EPROM, EEPROM, and flash memory devices; magnetic disks such as internal hard disks and removable disks; magneto-optical disks; and CD-ROM and DVD-ROM disks. Non-volatile memory 806 may store various computer instructions including operating system instructions 812, communication instructions 815, application instructions 816, and application data 817. Operating system instructions 812 may include instructions for implementing an operating system (e.g., Mac OS®, Windows®, or Linux). The operating system may be multi-user, multiprocessing, multitasking, multithreading, real-time, and the like. Communication instructions 815 may include network communications instructions, for example, software for implementing communication protocols, such as TCP/IP, HTTP, Ethernet, telephony, etc. Application instructions 816 may include instructions for administering shock patterns using a mobile AED, connecting to law enforcement, displaying instructions for administering shock patterns using the mobile AED, and performing a self-rescue operation according to the systems and methods disclosed herein. For example, application instructions 816 may include instructions for components 110-112 described above in conjunction with FIG. 1.

Peripherals 808 may be included within server device 800 or operatively coupled to communicate with server device 800. Peripherals 808 may include, for example, network subsystem 818, input controller 820, and disk controller 822. Network subsystem 818 may include, for example, an Ethernet of WiFi adapter. Input controller 820 may be any known input device technology, including but not limited to a keyboard (including a virtual keyboard), mouse, track ball, and touch-sensitive pad or display. Disk controller 822 may include one or more mass storage devices for storing data files; such devices include magnetic disks, such as internal hard disks and removable disks; magneto-optical disks; and optical disks.

Figure 9:
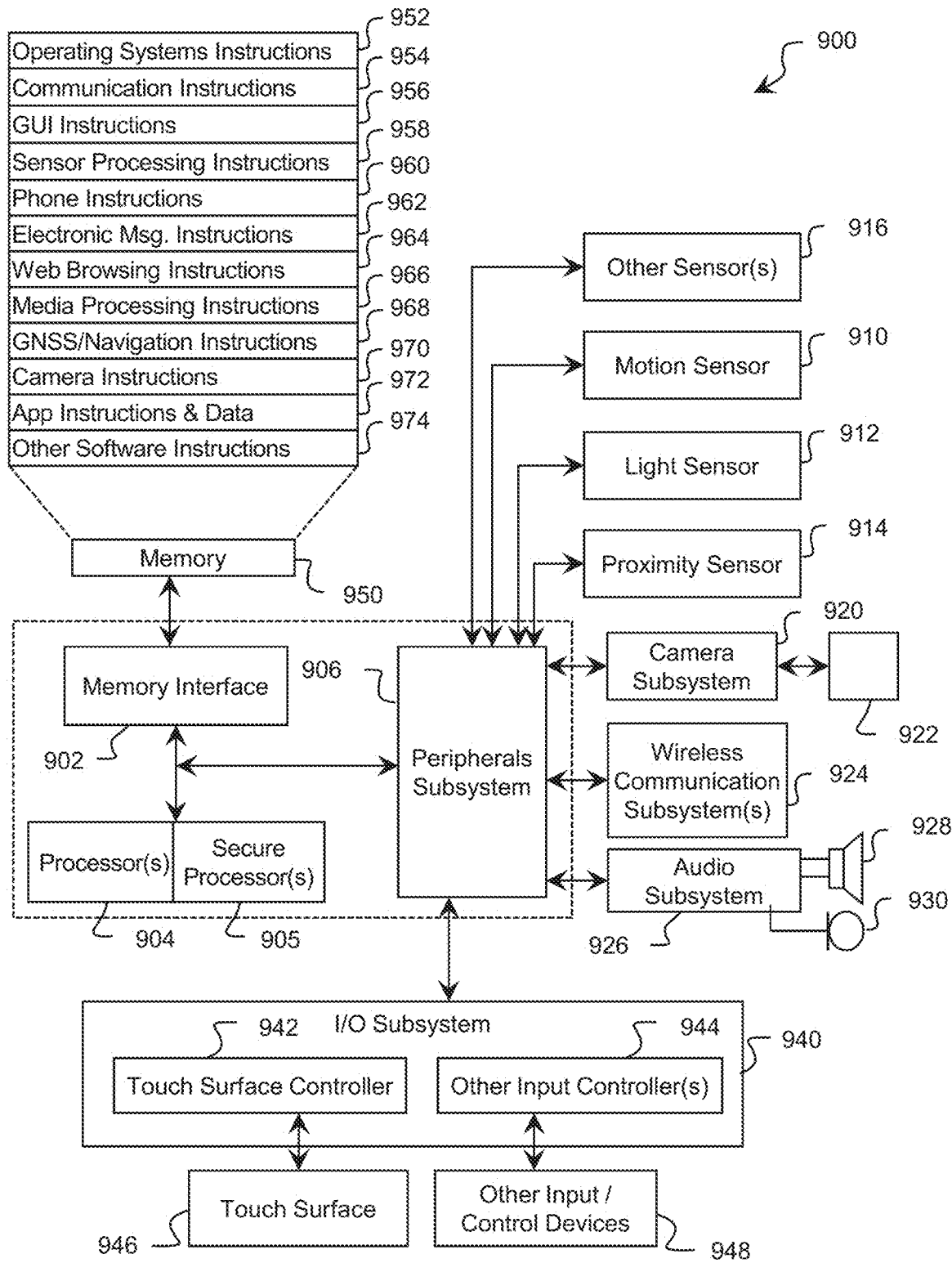
FIG. 9 is an example server device that can be used within the system of FIG. 3, according to some embodiments of the present disclosure.

FIG. 9 is an example computing device 900 that can be used within the system of FIGS. 1 and/or 3, according to some embodiments of the present disclosure. In some embodiments, device 900 may be user device 101. The illustrative user device 900 may include a memory interface 902, one or more data processors, image processors, central processing units 904, and/or secure processing units 905, and peripherals subsystem 906. Memory interface 902, one or more processors 904 and/or secure processors 905, and/or peripherals subsystem 906 may be separate components or may be integrated in one or more integrated circuits. The various components in user device 900 may be coupled by one or more communication buses or signal lines.

Sensors, devices, and subsystems may be coupled to peripherals subsystem 906 to facilitate multiple functionalities. For example, motion sensor 910, light sensor 912, and proximity sensor 914 may be coupled to peripherals subsystem 906 to facilitate orientation, lighting, and proximity functions. Other sensors 916 may also be connected to peripherals subsystem 906, such as a global navigation satellite system (GNSS) (e.g., GPS receiver), a temperature sensor, a biometric sensor, magnetometer, or other sensing device, to facilitate related functionalities.

Camera subsystem 920 and optical sensor 922, e.g., a charged coupled device (CCD) or a complementary metal-oxide semiconductor (CMOS) optical sensor, may be utilized to facilitate camera functions, such as recording photographs and video clips. Camera subsystem 920 and optical sensor 922 may be used to collect images of a user to be used during authentication of a user, e.g., by performing facial recognition analysis.

Communication functions may be facilitated through one or more wired and/or wireless communication subsystems 924, which may include radio frequency receivers and transmitters and/or optical (e.g., infrared) receivers and transmitters. For example, the Bluetooth (e.g., Bluetooth low energy (BTLE)) and/or WiFi communications described herein may be handled by wireless communication subsystems 924. The specific design and implementation of communication subsystems 924 may depend on the communication network(s) over which the user device 900 is intended to operate. For example, user device 900 may include communication subsystems 924 designed to operate over a GSM network, a GPRS network, an EDGE network, a WiFi or WiMax network, and a Bluetooth™ network. For example, wireless communication subsystems 924 may include hosting protocols such that device 900 may be configured as a base station for other wireless devices and/or to provide a WiFi service.

Audio subsystem 926 may be coupled to speaker 928 and microphone 930 to facilitate voice-enabled functions, such as speaker recognition, voice replication, digital recording, and telephony functions. Audio subsystem 926 may be configured to facilitate processing voice commands, voice-printing, and voice authentication, for example.

I/O subsystem 940 may include a touch-surface controller 942 and/or other input controller(s) 944. Touch-surface controller 942 may be coupled to a touch surface 946. Touch-surface 946 and touch-surface controller 942 may, for example, detect contact and movement or break thereof using any of a plurality of touch sensitivity technologies, including but not limited to capacitive, resistive, infrared, and surface acoustic wave technologies, as well as other proximity sensor arrays or other elements for determining one or more points of contact with touch surface 946.

The other input controller(s) 944 may be coupled to other input/control devices 948, such as one or more buttons, rocker switches, thumb-wheel, infrared port, USB port, and/or a pointer device such as a stylus. The one or more buttons (not shown) may include an up/down button for volume control of speaker 928 and/or microphone 930.

In some implementations, a pressing of the button for a first duration may disengage a lock of touch-surface 946; and a pressing of the button for a second duration that is longer than the first duration may turn power to user device 900 on or off. Pressing the button for a third duration may activate a voice control, or voice command, module that enables the user to speak commands into microphone 930 to cause the device to execute the spoken command. The user may customize a functionality of one or more of the buttons. Touch-surface 946 may, for example, also be used to implement virtual or soft buttons and/or a keyboard.

In some implementations, user device 900 may present recorded audio and/or video files, such as MP3, AAC, and MPEG files. In some implementations, user device 900 may include the functionality of an MP3 player, such as an iPod™. User device 900 may, therefore, include a 36-pin connector and/or 8-pin connector that is compatible with the iPod. Other input/output and control devices may also be used.

Memory interface 902 may be coupled to memory 950. Memory 950 may include high-speed random access memory and/or non-volatile memory, such as one or more magnetic disk storage devices, one or more optical storage devices, and/or flash memory (e.g., NAND, NOR). Memory 950 may store an operating system 952, such as Darwin, RTXC, LINUX, UNIX, OS X, Windows, or an embedded operating system such as VxWorks.

Operating system 952 may include instructions for handling basic system services and for performing hardware dependent tasks. In some implementations, operating system 952 may be a kernel (e.g., UNIX kernel). In some implementations, operating system 952 may include instructions for performing voice authentication.

Memory 950 may also store communication instructions 954 to facilitate communicating with one or more additional devices, one or more computers and/or one or more servers. Memory 950 may include graphical user interface instructions 956 to facilitate graphic user interface processing; sensor processing instructions 958 to facilitate sensor-related processing and functions; phone instructions 960 to facilitate phone-related processes and functions; electronic messaging instructions 962 to facilitate electronic messaging-related process and functions; web browsing instructions 964 to facilitate web browsing-related processes and functions; media processing instructions 966 to facilitate media processing-related functions and processes; GNSS/Navigation instructions 968 to facilitate GNSS and navigation-related processes and instructions; and/or camera instructions 970 to facilitate camera-related processes and functions.

Memory 950 may store application (or "app") instructions and data 972, such as instructions for the apps described above in the context of FIGS. 1-9. Memory 950 may also store other software instructions 974 for various other software applications in place on device 900.

In the foregoing specification, specific embodiments have been described. However, one of ordinary skill in the art appreciates that various modifications and changes can be made without departing from the scope of the invention as set forth in the claims below. For example, although the invention has been described and illustrated in connection with a school, it is not intended to be so limited. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

It is to be understood that the disclosed subject matter is not limited in its application to the details of construction and to the arrangements of the components set forth in the following description or illustrated in the drawings. The disclosed subject matter is capable of other embodiments and of being practiced and carried out in various ways. Also, it is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods, and systems for carrying out the several purposes of the disclosed subject matter. It is important, therefore, that the claims be regarded as including such equivalent constructions insofar as they do not depart from the spirit and scope of the disclosed subject matter.

Although the disclosed subject matter has been described and illustrated in the foregoing illustrative embodiments, it is understood that the present disclosure has been made only by way of example, and that numerous changes in the details of implementation of the disclosed subject matter may be made without departing from the spirit and scope of the disclosed subject matter.

The invention claimed is:

1. A method, performed by one or more processors of a device capable of running an application, for controlling a mobile defibrillator (AED) unit operatively connected to the device, the method comprising:
   detecting a connection of the mobile AED unit to the device;
   detecting that one or more electrodes of the mobile AED have been connected to a subject;
   receiving EKG measurements of the subject recorded by the one or more electrodes;
   receiving measured chest movement data by measuring movements of a chest of the subject;
   analyzing the chest movement data to determine a breathing pattern of the subject, wherein analyzing the chest movement data to determine the breathing pattern of the subject comprises:
      modeling the movements of the chest; and
      analyzing a breathing frequency;
   determining that the breathing pattern is a non-normal breathing pattern; and
   based on the determined non-normal breathing pattern, initiating a CPR protocol.

2. The method of claim 1, wherein initiating the CPR protocol comprises displaying instructions on the device to a user to provide CPR to the subject.

3. The method of claim 1 comprising, wherein the received measured breathing data is first measured breathing data:
   receiving second measured breathing data while CPR is being performed on the subject;
   analyzing the second measured breathing data to determine a frequency and force of pushing; and
   displaying a recommendation on the user device to change at least one of the frequency and the force of pushing.

4. The method of claim 1 comprising:
   determining that the breathing frequency is greater or less than a pre-defined breathing range; and
   in response to the determining, initiating the CPR protocol.

5. The method of claim 4, wherein the pre-defined breathing ranges is about ten to twenty breaths per minute.

6. The method of claim 1, wherein initiating the CPR protocol comprises displaying at least one of a video or instructions.

7. The method of claim 1, wherein initiating the CPR protocol comprises initiating a connection to a video specialist.

8. The method of claim 1 comprising:
   determining, based on the determined breathing pattern and the EKG measurements, an electrical shock pattern for administering to the subject; and
   administering the electrical shock pattern to the subject in conjunction with the CPR protocol.

9. The method of claim 8 comprising:
   providing a warning before or during the administering of the electrical shock pattern; and
   indicating that it is safe to perform a chest compression upon completion of the electrical shock pattern.

10. The method of claim 1 comprising:
    analyzing the breathing data to detect a rhythm at which cardiac compressions are being performed; and
    displaying feedback on the device associated with at least one of a frequency and force of the cardiac compressions.

11. The method of claim 1 comprising, in response to initiating the CPR protocol, transmitting a notification to at least one of law enforcement or emergency personnel.

12. A computing device comprising one or more processors and configured to operatively connect to and control a mobile defibrillator (AED) unit, wherein the computing device is configured to, via the one or more processors:
    detect a connection of the mobile AED unit;
    detect that one or more electrodes of the mobile AED have been connected to a subject;
    receive EKG measurements of the subject recorded by the one or more electrodes;
    receive measured breathing data associated with breathing movements of a chest of the subject;
    analyze the breathing data to determine a breathing pattern of the subject, wherein analyzing the breathing data to determine the breathing pattern of the subject comprises:
       modeling the movements of the chest; and
       analyzing a breathing frequency;
    determine that the breathing pattern is a non-normal breathing pattern; and
    based on the determined non-normal breathing pattern, initiate a CPR protocol.

13. The computing device of claim 12 comprising, wherein the received measured breathing data is first measured breathing data:

receiving second measured breathing data while CPR is being performed on the subject;

analyzing the second measured breathing data to determine a frequency and force of pushing; and displaying a recommendation on the user device to change at least one of the frequency and the force of pushing.

14. The method of claim 12 comprising:

determining that the breathing frequency is greater or less than a pre-defined breathing range; and in response to the determining, initiating the CPR protocol.

15. The method of claim 14, wherein the pre-defined breathing ranges is about ten to twenty breaths per minute.

16. The computing device of claim 12 comprising:

determining, based on the determined breathing pattern and the EKG measurements, an electrical shock pattern for administering to the subject; and administering the electrical shock pattern to the subject in conjunction with the CPR protocol.

17. The computing device of claim 16 comprising:

providing a warning before or during the administering of the electrical shock pattern; and indicating that it is safe to perform a chest compression upon completion of the electrical shock pattern.

18. The method of computing device of claim 12 comprising:

analyzing the breathing data to detect a rhythm at which cardiac compressions are being performed; and displaying feedback on the device associated with at least one of a frequency and force of the cardiac compressions.

\* \* \* \* \*